(12) United States Patent
Frieding et al.

(10) Patent No.: US 11,924,612 B2
(45) Date of Patent: Mar. 5, 2024

(54) DISTRACTION REMEDIATION AT A HEARING DEVICE

(71) Applicant: Cochlear Limited, Macquarie University (AU)

(72) Inventors: Jan Patrick Frieding, Grose Vale (AU); Ryan Orin Melman, South Coogee (AU)

(73) Assignee: Cochlear Limited, Macquarie University (AU)

( * ) Notice: Subject to any disclaimer, the term of this patent is extended or adjusted under 35 U.S.C. 154(b) by 0 days.

(21) Appl. No.: 16/753,640

(22) PCT Filed: Sep. 25, 2018

(86) PCT No.: PCT/IB2018/057409
§ 371 (c)(1),
(2) Date: Apr. 3, 2020

(87) PCT Pub. No.: WO2019/069175
PCT Pub. Date: Apr. 11, 2019

(65) Prior Publication Data
US 2020/0252730 A1 Aug. 6, 2020

Related U.S. Application Data

(60) Provisional application No. 62/568,406, filed on Oct. 5, 2017.

(51) Int. Cl.
*H04R 25/00* (2006.01)
*A61B 5/12* (2006.01)
(Continued)

(52) U.S. Cl.
CPC .............. *H04R 25/30* (2013.01); *A61B 5/125* (2013.01); *A61B 5/38* (2021.01); *H04R 1/10* (2013.01);
(Continued)

(58) Field of Classification Search
CPC .... H04R 1/1083; H04R 1/1091; H04R 25/30; H04R 1/10; H04R 25/70; A61B 5/12;
(Continued)

(56) References Cited

U.S. PATENT DOCUMENTS 6,118,877 A * 9/2000 Lindemann ............ H04R 25/70
381/23.1
6,160,893 A 12/2000 Saunders
(Continued)

FOREIGN PATENT DOCUMENTS

CN 102105192 A 6/2011
CN 102215796 A 10/2011
(Continued)

OTHER PUBLICATIONS

Hiu et al., Hearing Screening for school children utility of noise cancelling headphones, (Year: 2013).*
(Continued)

*Primary Examiner* — Carolyn R Edwards
*Assistant Examiner* — Kuassi A Ganmavo
(74) *Attorney, Agent, or Firm* — Edell, Shapiro & Finnan, LLC

(57) ABSTRACT

Presented herein are integrated techniques to address the perception of distracting sounds by a recipient's residual hearing during testing of a hearing prosthesis. More specifically, in accordance with embodiments presented herein, a first hearing prosthesis located at a first ear of a recipient is configured to selectively operate in a testing-assistance mode in order to support or supplement the testing of testing of the first hearing prosthesis or a second hearing prosthesis located at a second ear of the recipient.

14 Claims, 8 Drawing Sheets

(51) Int. Cl.
*A61B 5/38* (2021.01)
*A61F 11/08* (2006.01)
*G10K 11/178* (2006.01)
*H04R 1/10* (2006.01)

(52) U.S. Cl.
CPC .............. *H04R 25/70* (2013.01); *A61B 5/123* (2013.01); *A61F 11/08* (2013.01); *G10K 11/178* (2013.01); *G10K 2210/1081* (2013.01); *H04R 1/1083* (2013.01); *H04R 1/1091* (2013.01)

(58) Field of Classification Search
CPC ........... A61B 5/121; A61B 5/123; A61B 5/38; A61B 5/125; A61B 5/7203; A61F 11/08; A61F 2011/145; G10K 2210/1081; G10K 11/178
See application file for complete search history.

(56) References Cited

U.S. PATENT DOCUMENTS

| | | | | |
|---|---|---|---|---|
| 6,396,930 | B1* | 5/2002 | Vaudrey | A61B 5/121 381/60 |
| 6,496,585 | B1* | 12/2002 | Margolis | A61B 5/121 381/60 |
| 6,532,296 | B1* | 3/2003 | Vaudrey | G10K 11/17885 381/371 |
| 7,018,342 | B2* | 3/2006 | Harrison | H04R 25/606 600/559 |
| 8,298,155 | B2 | 10/2012 | Lee | |
| 8,649,538 | B2 | 2/2014 | Apfel | |
| 9,326,706 | B2 | 5/2016 | Shennib | |
| 9,554,733 | B2 | 1/2017 | Henriksen | |
| 2002/0176584 | A1* | 11/2002 | Kates | H04R 25/453 381/60 |
| 2002/0183648 | A1 | 12/2002 | Hou | |
| 2004/0037428 | A1* | 2/2004 | Keller | A61B 5/121 381/60 |
| 2004/0097826 | A1* | 5/2004 | Harrison | A61B 5/742 600/559 |
| 2007/0076909 | A1* | 4/2007 | Roeck | H04R 25/70 381/312 |
| 2007/0195977 | A1 | 8/2007 | Fink et al. | |
| 2007/0204695 | A1* | 9/2007 | Gross | A61B 5/6888 73/1.82 |
| 2007/0206825 | A1* | 9/2007 | Thomasson | H04R 25/407 381/317 |
| 2009/0041260 | A1* | 2/2009 | Jorgensen | G10K 11/17885 381/71.6 |
| 2009/0074197 | A1* | 3/2009 | Neher | H04R 25/70 381/60 |
| 2009/0116657 | A1 | 5/2009 | Edwards | |
| 2010/0030012 | A1 | 2/2010 | Meskens | |
| 2010/0210896 | A1* | 8/2010 | Davis | H04R 25/505 600/28 |
| 2010/0268115 | A1* | 10/2010 | Wasden | A61B 5/121 600/559 |
| 2011/0293124 | A1* | 12/2011 | Ma | H04R 25/70 381/318 |
| 2012/0029383 | A1* | 2/2012 | Henriksen | A61F 11/08 600/559 |
| 2012/0029594 | A1* | 2/2012 | Chapa | H04R 25/70 607/57 |
| 2012/0076313 | A1* | 3/2012 | Junius | A61B 5/126 381/60 |
| 2012/0130271 | A1* | 5/2012 | Margolis | A61B 5/123 600/559 |
| 2012/0203130 | A1* | 8/2012 | Bernhard | A61B 5/389 600/544 |
| 2012/0283593 | A1* | 11/2012 | Searchfield | H04R 25/75 381/17 |
| 2013/0303940 | A1* | 11/2013 | Saly | A61B 5/123 600/559 |
| 2014/0128940 | A1* | 5/2014 | Strahl | A61N 1/36039 607/57 |
| 2014/0257131 | A1* | 9/2014 | Polley | A61B 5/744 600/28 |
| 2015/0025413 | A1* | 1/2015 | Shennib | A61B 5/123 600/559 |
| 2015/0264492 | A1 | 9/2015 | Laudanski | |
| 2015/0341731 | A1 | 11/2015 | Polak | |
| 2015/0358745 | A1* | 12/2015 | Rix | G10K 11/16 381/60 |
| 2016/0157029 | A1* | 6/2016 | Zhang | G10K 11/17827 381/317 |
| 2016/0166181 | A1* | 6/2016 | Shennib | H04R 25/305 600/559 |
| 2018/0063618 | A1* | 3/2018 | Boesen | H04R 1/10 |

FOREIGN PATENT DOCUMENTS

| | | |
|---|---|---|
| CN | 104284288 A | 1/2015 |
| WO | 2001006916 A1 | 2/2001 |
| WO | 2008139404 A1 | 11/2008 |

OTHER PUBLICATIONS

International Search Report and Written Opinion received in related application PCT/IB2018/057409, dated Jan. 16, 2019 (7 pages).

* cited by examiner

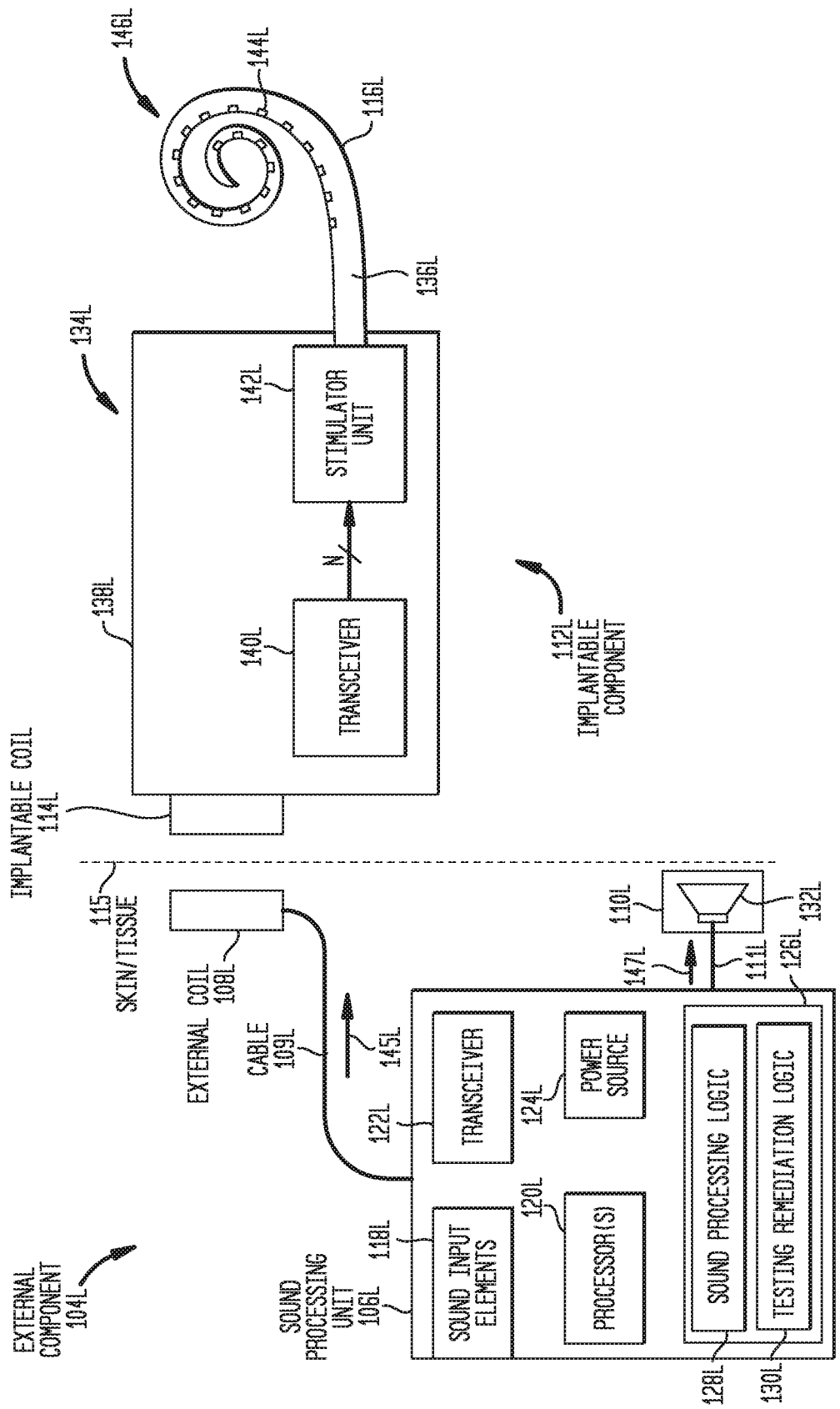

DISTRACTION REMEDIATION AT A HEARING DEVICE

BACKGROUND

Field of the Invention

The present invention relates generally to remediation of distracting sounds at a hearing prosthesis.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, to the nerve pathways from the inner ear to the brain, or the brain itself.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to, for example, damage to the auditory nerve.

Certain individuals suffer from only partial sensorineural hearing loss and, as such, retain at least some residual hearing. These individuals may be candidates for electro-acoustic hearing prostheses.

SUMMARY

In one aspect presented herein, a method is provided. The method comprises: receiving a first set of sound signals at one or more sound inputs of a first hearing prosthesis located at a first ear of a recipient; operating the first hearing prosthesis in a sound processing mode to convert the first set of sound signals into output signals for use in stimulating a first ear of a recipient; detecting, at the first hearing prosthesis, initiation of a testing-assistance mode; delivering test stimulation to at least one of the first or a second ear of the recipient; and while operating in the testing-assistance mode, remediating, by the first hearing prosthesis, distracting sounds perceived by a first one of the first or second ears of the recipient during the delivery of test stimulation to the at least one of the first or second ear of the recipient.

In another aspect presented herein, a method is provided. The method comprises: delivering test stimulation to a first ear of a recipient, wherein a first hearing prosthesis is located at the first ear of the recipient; detecting, a presence of one or more distracting sounds at a first one of the first or a second ear of the recipient, where the first one of the first or second ears of the recipient has residual hearing; and delivering testing remediation stimulation to the first one of the first or second ears of the recipient, wherein the testing remediation stimulation is delivered concurrently with the test stimulation and is configured to at least reduce the effect of the presence of one or more distracting sounds at the first one of the first or second ears on a perception of the test stimulation by the recipient via the first ear.

In another aspect presented herein, a hearing prosthesis is provided. The hearing prosthesis comprises: one or more sound inputs; one or more processors configured to: operate in a sound processing mode to convert sound signals received at the one or more sound inputs into output signals for use in stimulating a first ear of a recipient, and selectively operate in a testing-assistance mode to perform one or more testing remediation operations to support the testing of a hearing prosthesis located at a second ear of the recipient.

BRIEF DESCRIPTION OF THE DRAWINGS

Embodiments of the present invention are described herein in conjunction with the accompanying drawings, in which:

FIG. 1D is a block diagram of one hearing prosthesis forming part of the bilateral hearing prosthesis system of FIG. 1A;

DETAILED DESCRIPTION

Figure 1A:
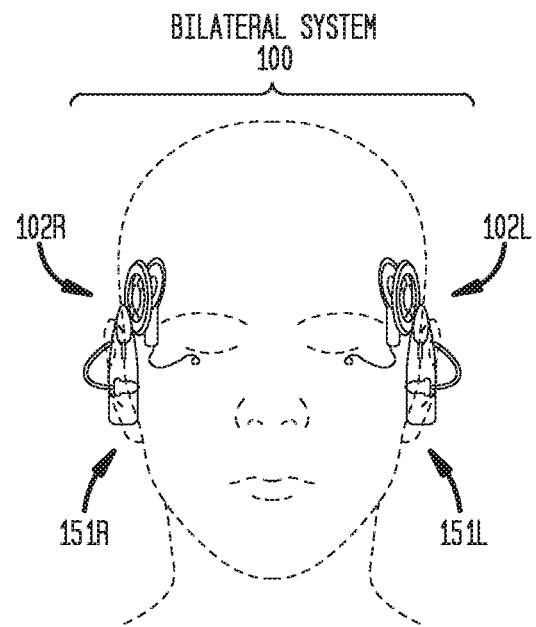
FIG. 1A is a schematic view of a bilateral hearing prosthesis system in which embodiments presented herein may be implemented.

An auditory or hearing prosthesis system includes one or more auditory/hearing prostheses that are each configured to convert sound signals into one or more of acoustic, mechanical, and/or electrical stimulation signals for delivery to a recipient. The one or more hearing prostheses that can form part of a hearing prosthesis system include, for example, hearing aids, cochlear implants, middle ear stimulators, bone conduction devices, brain stem implants, electro-acoustic devices, and other devices providing acoustic, mechanical, and/or electrical stimulation to a recipient.

Hearing prosthesis recipients suffer from different types of hearing loss (e.g., conductive and/or sensorineural) and/or different degrees/severity of hearing loss. A particular hearing prosthesis recipient may also experience different types/degrees of hearing losses in each of his/her ears (i.e., sensorineural loss in the first ear, conductive hearing loss the second ear; severe sensorineural loss in the first ear, mild or moderate sensorineural loss in the second ear, or other various hearing loss combinations). Even with cochlear implant recipients, it is now common for the recipients to retain some residual natural hearing ability (residual hearing) after receiving the cochlear implant. For example, progressive improvements in the design of intra-cochlear electrode arrays (stimulating assemblies), surgical implantation techniques, tooling, etc. have enabled atraumatic surgeries which preserve at least some of the recipient's fine inner ear structures (e.g., cochlea hair cells) and the natural cochlea function, particularly in the lower frequency regions of the cochlea.

The benefits of residual hearing (i.e., the ability to naturally hear some sounds even if a hearing loss exists) are numerous. In particular, the cochlea includes a large number of hair cells (e.g., approximately 20,000 hair cells) that convert movement of the cochlea fluid into electrical nerve pulses that are perceived as sound. With residual hearing, some of the hair cells are operational (i.e., are neither missing not damaged) so as to be able to respond to certain sound frequencies, thereby enabling the recipient to naturally perceive those sound frequencies. Residual hearing can, in some cases, also provide improved pitch and music perception and/or appreciation, as the acoustic signals may contain a more salient lower frequency (e.g., fundamental pitch, F0) representation than is possible with electrical stimulation. Other benefits of residual hearing may include, for example, improved sound localization, binaural release from unmasking, the ability to distinguish acoustic signals in a noisy environment, better music appreciation, etc.

In many cases, the effectiveness of a hearing prosthesis depends on how well the prosthesis is configured or "fit" to the recipient of the particular prosthesis. The "fitting" of a hearing prosthesis to a recipient, sometimes also referred to as "programming" or "mapping," creates a set of configuration settings and other data that defines the specific operational characteristics of the hearing prosthesis. In general, fitting determines how the hearing prosthesis operates to convert detected sound signals (sounds) into stimulation signals that are delivered to the recipient's ear (e.g., inner, middle, or outer ear).

Hearing prosthesis fitting often includes the delivery of test stimulation to the recipient via the hearing prosthesis. Subjective and/or objective feedback is then elicited from the recipient and used to set the operational characteristics of the hearing prosthesis. It is also common for recipients to participate in a number of fitting or other types of testing sessions over the life-time of the hearing prosthesis to ensure, for example, that the prosthesis is operating properly, the recipient's hearing loss has not changed, impedances have not changed, etc.

As noted, in terms of sound perception, residual hearing is beneficial for many hearing prosthesis recipients. However, residual hearing may also be problematic when testing or evaluating the operation of a hearing prosthesis (e.g., during a fitting or other type of testing session). In particular, the residual hearing may perceive/detect sounds that distract from, or are otherwise a detriment to, the testing of the hearing prosthesis. These sounds, which are sometimes referred to herein as "detrimental" or "distracting" sounds, may include, for example, ambient/background noise, tinnitus sounds, or testing sounds (e.g., natural detection of free-field signals presented to the hearing prosthesis) presented at/on the other side of the head. The natural perception of these distracting sounds via the residual hearing may negatively affect, interfere with, or otherwise alter the results of the hearing prosthesis testing process.

Although the perception of distracting sounds may occur in a number of different manners, two primary issues relate to ambient noise and cross hearing. Ambient noise refers to noise sounds that are present in the testing environment (i.e., in the physical area in which the hearing prosthesis testing is conducted). For example, if ambient noise levels are too high, then the test stimulation can be partially masked and it will appear that the recipient's threshold level is higher than it would be in a quieter environment. Cross hearing refers to the situation in which the recipient has residual hearing in the non-tested ear that can also perceive the testing stimulation.

Conventional solutions to address the perception of distracting sounds by a recipient's residual hearing are unsatisfactory for a number of reasons, including that the conventional solutions rely on costly third-party testing requirement (i.e., the solutions are not integrated into a hearing prosthesis system), are not reliable in application, are highly reliant on skilled testers (e.g., clinicians/audiologists) that have intimate knowledge of the operation of the testing equipment, and do not address the needs for testing outside of a clinical setting. As such, there is a need for improved systems and methods to ensure that the perception of distracting sounds by a recipient's residual hearing does not interfere with the testing of a hearing prosthesis.

Presented herein are integrated techniques to address the perception of distracting sounds by a recipient's residual hearing during testing of a contralateral and/or ipsilateral hearing prosthesis. More specifically, in accordance with embodiments presented herein, a first hearing prosthesis located at a first ear of a recipient is configured to selectively operate in a "testing-assistance" mode in order to support or supplement the testing of the first hearing prosthesis (i.e., ipsilateral remediation) or to support or supplement the testing of a second hearing prosthesis located at a second ear of the recipient (i.e., contralateral remediation). While operating in the testing-assistance mode, the first hearing prosthesis performs one or more operations to remediate the perception of the distracting sounds received/detected at the first and/or second hearing prosthesis. In presence of residual hearing, the one or more operations, sometimes referred to herein as "remediation" operations, at least reduce the effect of distracting sounds on the testing process. As described further below, the remediation operations are integrated within a hearing prosthesis and do not require a separate device to perform the remediation operations.

As described further below, the techniques presented herein may be used in a wide variety of testing conditions, including free-field test (i.e., testing hearing recipient responses on hearing aided with a hearing prosthesis), central testing (i.e., testing unaided responses that can be centrally activated, such as Stapedius Reflex tests, central language tests, etc.), remote testing (i.e., testing outside of the clinical setting, even in the presence of distracting ipsilateral or contralateral tinnitus noise, in the presence of uncontrolled ambient noise, or for administering rehabilitation regimes, such as hearing exercises with a prosthesis). For any of the above testing conditions, the contralateral and/or ipsilateral ear may need to be remediated, if it still has residual hearing, residual hearing is unknown or cannot be excluded, or if tinnitus noise or single-sided deafness are present. This is needed to ensure only the ear and prosthesis under test are assessed and one or both ears are not perceiving distracting sounds.

For ease of illustration, embodiments are primarily described herein with reference to hearing prosthesis systems that include two hearing prostheses, one prosthesis located at each ear of the recipient (e.g., bilateral systems, bi-modal systems, etc.). In such systems, each of the two hearing prostheses provides stimulation to one of the two ears of the recipient (i.e., either the right or the left ear of the recipient). The hearing prostheses in such systems may include, for example, hearing aids, cochlear implants, middle ear stimulators, bone conduction devices, brain stem implants, electro-acoustic devices, and other devices providing acoustic, mechanical, and/or electrical stimulation to a recipient. In addition, as described further below, the hearing prostheses in such systems may be operationally linked to provide treatment to the recipient or may be two stand-alone prostheses (e.g., in a clinical setting where a first prosthesis is used to perform remediation operations described herein and the second hearing prosthesis provides treatment to a single ear, such as in the case of single-sided deafness.

Figure 1B:
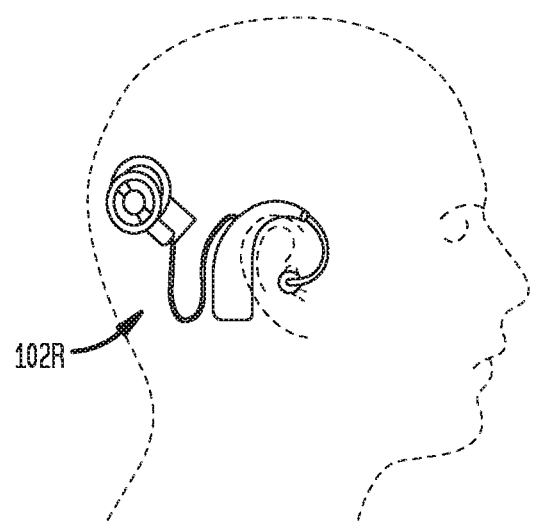
FIG. 1B is a side view of a recipient wearing the bilateral hearing prosthesis system of FIG. 1A.
Figure 1C:
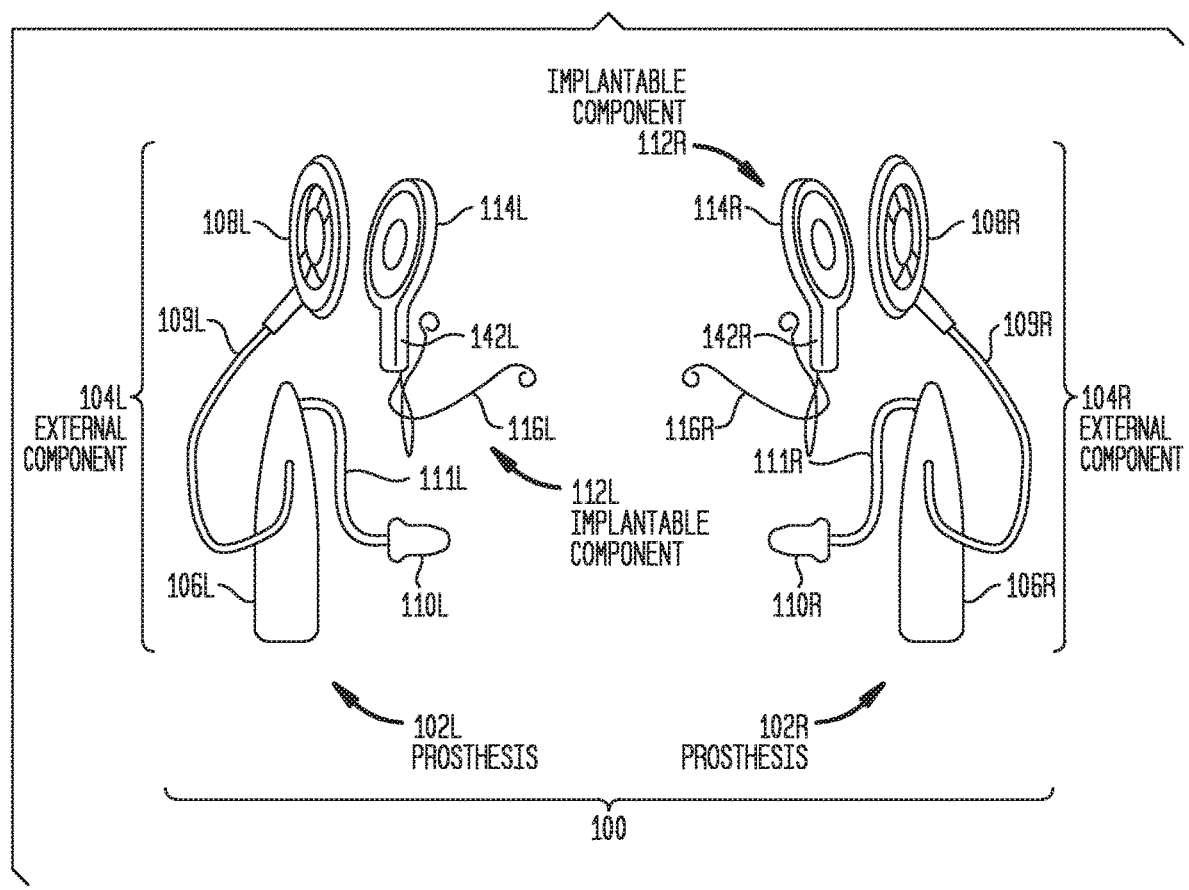
FIG. 1C is a schematic view of the components of the bilateral hearing prosthesis system of FIG. 1A.

FIGS. 1A, 1B, 1C, and 1D are diagrams illustrating one example hearing prosthesis system 100 configured to implement the integrated testing remediation techniques presented herein. More specifically. FIGS. 1A, 1B, 1C, and 1D illustrate an example bilateral system 100 comprising two electro-acoustic hearing prostheses, referred to as electro-acoustic hearing prosthesis 102L and electro-acoustic hearing prosthesis 102R. FIGS. 1A and 1B are schematic drawings of a recipient wearing the left electro-acoustic hearing prosthesis 102L at a left ear 151L and the right electro-acoustic hearing prosthesis 102R at a right ear 151R, while FIG. 1C is a schematic view illustrating further details of each of the left and right hearing prostheses. FIG. 1D is a block diagram illustrating further details of the left hearing prosthesis 102L.

Referring specifically to FIG. 1C, electro-acoustic hearing prosthesis 102L includes an external component 104L that is configured to be directly or indirectly attached to the body of the recipient. The external component 104L comprises a sound processing unit 106L that is electrically connected to an external coil 108L via cable 109L. The external component 104L also comprises a hearing aid component 110L that is electrically connected to the sound processing unit 106L via a cable 111L.

Electro-acoustic hearing prosthesis 102L also includes implantable component 112L implanted in the recipient. Implantable component 112L includes an internal coil 114L, a stimulator unit 115L and an elongate stimulating assembly (electrode array) 116L implanted in the recipient's left cochlea (not shown in FIG. 1C).

The electro-acoustic hearing prosthesis 102R is substantially similar to electro-acoustic hearing prosthesis 102L. In particular, electro-acoustic hearing prosthesis 102R includes an external component 104R comprising a sound processing unit 106R, an external coil 108R, a first cable 109R, a hearing aid component 11R, and a second cable 111R. Electro-acoustic hearing prosthesis 102R also includes an implantable component 112R comprising internal coil 114R, stimulator unit 115R, and elongate stimulating assembly 116R.

FIG. 1D is a block diagram illustrating further details of electro-acoustic hearing prosthesis 102L. As noted, electro-acoustic hearing prosthesis 102R is substantially similar to electro-acoustic hearing prosthesis 102L and, as such, further details of electro-acoustic hearing prosthesis 102R have been omitted. Although these illustrative embodiments include two electro-acoustic hearing prostheses, it is to be appreciated that embodiments presented herein may be implemented in systems that include other combination of prostheses, such as a cochlear implant at one ear and a hearing aid at the second ear. Alternatively, the electro-acoustic hearing prostheses 102L and 102R could each be implemented as a combination of a cochlear implant and a hearing aid.

As noted, the external component 104L of the electro-acoustic hearing prosthesis 102L includes a sound processing unit 106L. The sound processing unit 106L comprises one or more sound input elements 118L (e.g., microphones, audio input ports, cable ports, telecoils, a wireless transceiver, etc.), one or more processors 120L, an external transceiver unit (transceiver) 122L, a power source 124L, and a memory 126L that includes sound processing logic 128L, and testing remediation logic 130L. The sound processing unit 106L may be, for example, a behind-the-ear (BTE) sound processing unit, a body-worn sound processing unit, a button sound processing unit, etc.

As noted, connected to the sound processing unit 106L is a hearing aid component 110L. The hearing aid component 110L includes a receiver 132L that may be, for example, positioned in or near the recipient's outer car. The receiver 132L is an acoustic transducer that is configured to deliver acoustic signals (acoustical stimulation signals) to the recipient via the recipient's ear canal and middle ear.

The implantable component 112L comprises an implant body (main module) 134L, a lead region 136L, and the intra-cochlear stimulating assembly 116L, all configured to be implanted under the skin/tissue (tissue) 115 of the recipient. The implant body 134L generally comprises a hermetically-sealed housing 138L in which an internal transceiver unit (transceiver) 140L and a stimulator unit 142L are disposed. The implant body 134L also includes the internal/implantable coil 114L that is generally external to the housing 138L, but which is connected to the transceiver 140L via a hermetic feedthrough (not shown in FIG. 1D).

As noted, stimulating assembly 116L is configured to be at least partially implanted in the recipient's cochlea. Stimulating assembly 116L includes a plurality of longitudinally spaced intra-cochlear electrical stimulating contacts (electrodes) 144L that collectively form a contact or electrode array 146L for delivery of electrical stimulation (current) to the recipient's cochlea.

Stimulating assembly 116L extends through an opening in the recipient's cochlea (e.g., cochleostomy, the round window, etc.) and has a proximal end connected to stimulator unit 142L via lead region 136L and a hermetic feedthrough (not shown in FIG. 1D). Lead region 136L includes a plurality of conductors (wires) that electrically couple the electrodes 144L to the stimulator unit 142L.

As noted, the electro-acoustic hearing prosthesis 102L includes the external coil 108L and the implantable coil 114L. The coils 108L and 114L are typically wire antenna coils each comprised of multiple turns of electrically insulated single-strand or multi-strand platinum or gold wire. Generally, a magnet is fixed relative to each of the external coil 108L and the implantable coil 114L. The magnets fixed relative to the external coil 108L and the implantable coil 114L facilitate the operational alignment of the external coil 108L with the implantable coil 114L. This operational alignment of the coils enables the external component 104L to transmit data, as well as possibly power, to the implantable component 112L. In certain examples, external coil 108L transmits data and/or power to implantable coil 114L via a radio frequency (RF) link. However, various other types of energy transfer, such as infrared (IR), electromagnetic, capacitive and inductive transfer, may be used to transfer the power and/or data from an external component to an implantable component and, as such, FIG. 1D illustrates only one example arrangement.

In operation, the sound input element(s) 118L are configured to detect/receive input sound signals and to generate electrical input signals therefrom. The one or more processors 120L are configured to execute sound processing logic 128L in memory 126L to convert the input signals received from the sound input element(s) 118L into data signals that represent acoustical and/or electrical stimulation for delivery to the recipient. That is, the electro-acoustic hearing prosthesis 102L operates to evoke perception by the recipient of sound signals received by the sound input element(s) 118L through the delivery of one or both of electrical stimulation signals and acoustical stimulation signals to the recipient. As such, depending on a variety of factors, the one or more processors 120L (executing sound processing logic 128L) are configured to convert the input signals received from the sound input element(s) 118L into a first set of output signals representative of electrical stimulation and/or into a second set of output signals representative of acoustical stimulation. The output signals representative of electrical stimulation are represented in FIG. 1D by arrow 145L, while the output signals representative of acoustical stimulation are represented in FIG. 1D by arrow 147L.

The output signals 145L are provided to the transceiver 114, which transcutaneously transfers the output signals 145L (e.g., in an encoded manner) to the implantable component 112L via external coil 108L and implantable coil 114L. That is, the output signals 145L are received at the transceiver 140L via implantable coil 114L and provided to the stimulator unit 142L. The stimulator unit 142L is configured to utilize the output signals 145L to generate electrical stimulation signals (e.g., current signals) for delivery to the recipient's cochlea via one or more stimulating contacts 144L. In this way, electro-acoustic hearing prosthesis 102L electrically stimulates the recipient's auditory nerve cells, bypassing absent or defective hair cells that normally transduce acoustic vibrations into neural activity, in a manner that causes the recipient to perceive one or more components of the received sound signals.

As noted above, the one or more processors 120L (executing sound processing logic 128L) may also generate output signals 147L representative of acoustical stimulation. These output signals 147L are provided to the receiver 132L, which is configured to utilize the output signals 147L to generate acoustical stimulation signals that are provided to the recipient. In other words, the electro-acoustic hearing prosthesis 102L is operable to enhance, and/or amplify a sound signal which is delivered to the cochlea via the middle ear bones and oval window, thereby creating waves of fluid motion of the perilymph within the cochlea. The acoustical stimulation makes use of residual hearing of the recipient in one or more frequency ranges.

The one or more processors 120L generate output signals 145L and 147L in accordance with various operating parameters/settings. The various operating parameters may be in the form of executable programs or sets of parameters for use in a program and form part of sound processing logic 128L. The settings may accommodate any of a number of specific configurations that influence the operation of the electro-acoustic hearing prosthesis 102L. For example, the operating parameters may include different digital signal and sound processing algorithms, processes and/or operational parameters for different algorithms, other types of executable programs (such as system configuration, user interface, etc.), or operational parameters for such programs. The operating parameters may also include different optimal settings for different listening situations or environments encountered by the recipient (i.e., noisy or quite environments, windy environments, or other uncontrolled noise environments).

Additionally, since the dynamic range for electrical stimulation is relatively narrow and varies across recipients and stimulating contacts, parameters used in sound processing are typically individually tailored to optimize the perceptions presented to a particular recipient (i.e., tailor the characteristics of electrical stimulation for each recipient). For example, many speech processing strategies rely on a customized set of stimulation settings which provide, for a particular recipient, the threshold levels (T-levels) and comfortable levels (C-levels) of stimulation for each frequency band. Once these stimulation settings are established, the processor(s) may then optimally process and convert the received sound signals into output signals for use in delivering electrical or acoustical stimulation signals to the recipient.

As such, it is clear that a typical electro-acoustic hearing prosthesis, or other types of hearing prostheses, have many parameters which determine the sound processing operations of the device. The individualized programs, commands, data, settings, parameters, instructions, and/or other information that define the specific characteristics used by a hearing prosthesis to process input signals and generate stimulation data therefrom are generally and collectively referred to as "sound processing settings." As noted above, the effectiveness of a hearing prosthesis depends on how well-suited these sound processing settings are for a particular recipient (i.e., how well the hearing prosthesis is fit to the recipient of the particular prosthesis).

As such, presented herein are techniques to ensure that a hearing prosthesis fitting or other testing session/process (collectively and general referring to herein as "hearing prosthesis testing sessions") is largely unaffected by distracting sounds, such as ambient/background noise, tinnitus noise, the test sounds (e.g., natural detection of the test sounds in the case of free-field testing), etc., that could be perceived by the recipient's residual hearing. More specifically, returning to the examples of FIGS. 1A-1D, it may be desired to test/evaluate the recipient's electro-acoustic hearing prosthesis 102L (i.e., the prosthesis located at the recipient's left ear) and/or the recipient's electro-acoustic hearing prosthesis 102R (i.e., the hearing prosthesis located the recipient's right ear). In accordance with embodiments presented, the electro-acoustic hearing prosthesis 102L and/or the electro-acoustic hearing prosthesis 102R can be configured to operate in a "testing-assistance" mode to perform remediation operations to facilitate the testing of either or both of the electro-acoustic hearing prostheses 102L or 102R.

As described elsewhere herein, a hearing prosthesis in accordance with embodiments presented herein may be configured to operate in a testing-assistance mode to perform either contralateral or ipsilateral remediation operations. Contralateral remediation operations refer to one or more operations configured to address residual hearing at the opposite ear (i.e., the contralateral ear) of the recipient. For example, with reference to the electro-acoustic hearing prosthesis 102L, contralateral remediation operations refer operations by the electro-acoustic hearing prosthesis 102L (e.g., active noise cancelling, ambient noise monitoring, etc.) that, in presence of residual hearing at the contralateral ear, at least reduce the effect of distracting sounds on the testing of the contralateral electro-acoustic hearing prosthesis 102R (i.e., the other prosthesis).

Figure 2A:
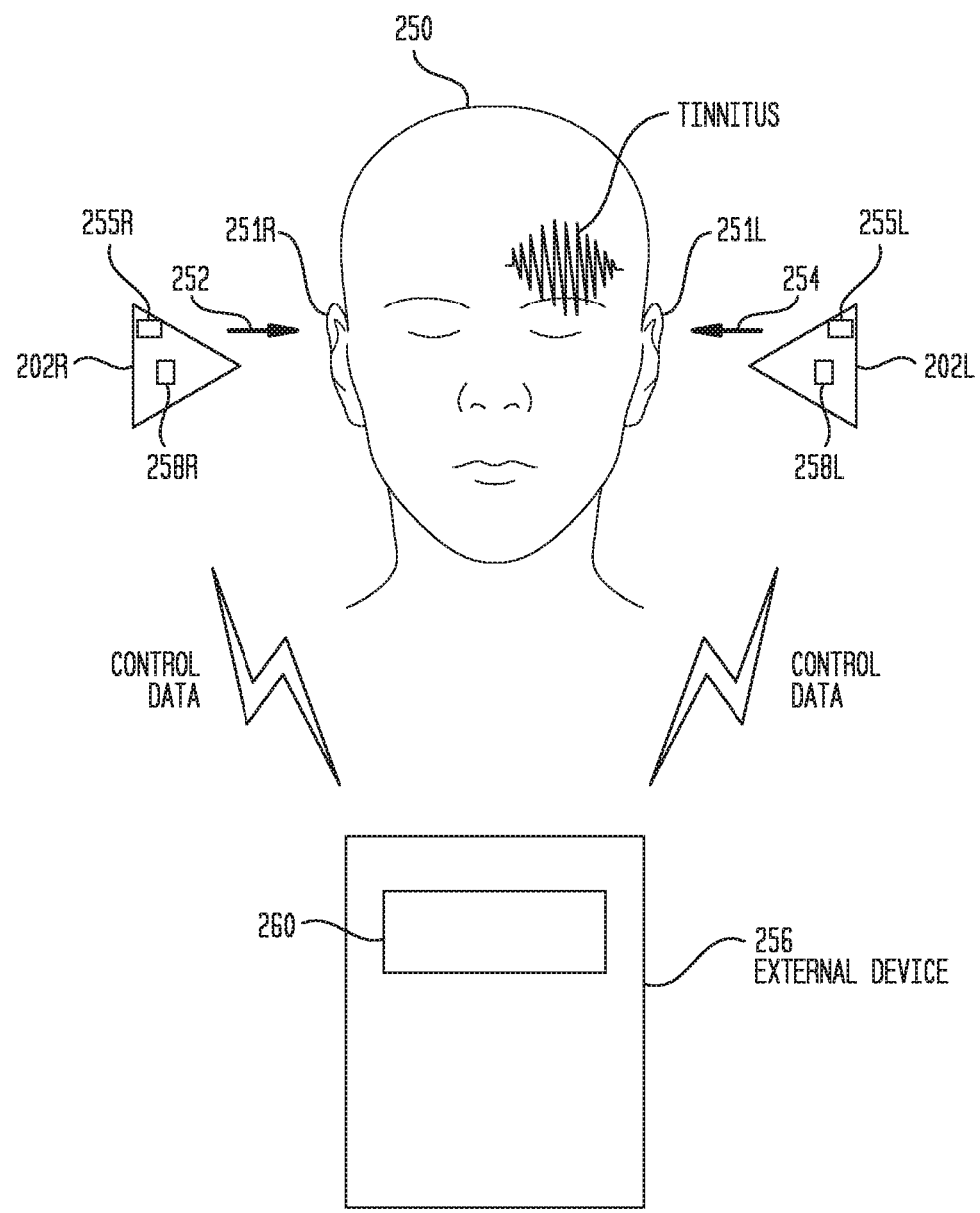
FIGS. 2A and 2B are a schematic diagram illustrating implementation of the techniques presented herein, according to certain embodiments.
Figure 2B:
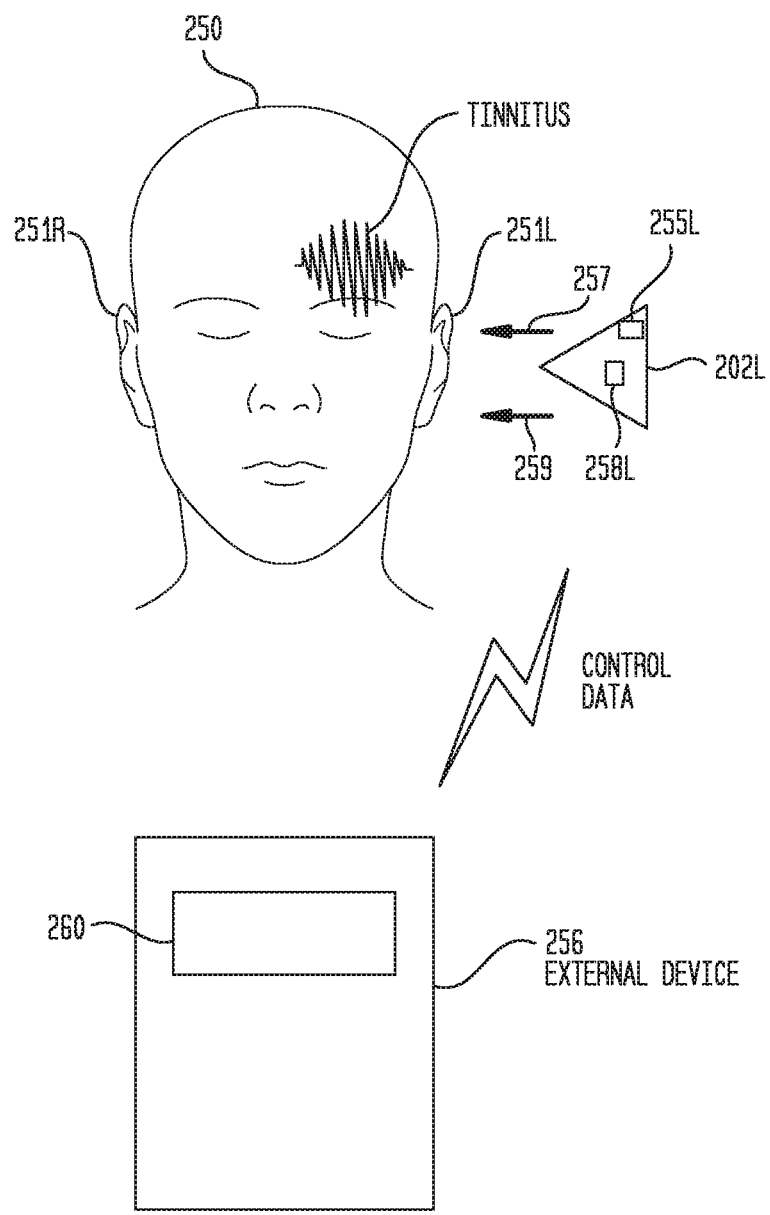

In contrast, ipsilateral remediation operations refer to one or more operations configured to address residual hearing at the same ear (i.e., the ipsilateral ear) of the recipient. For example, with reference to the electro-acoustic hearing prosthesis 102L, ipsilateral remediation operations refer operations by the electro-acoustic hearing prosthesis 102L (e.g., active noise cancelling, ambient noise monitoring, etc.) that, in presence of residual hearing at the ipsilateral ear, at least reduce the effect of distracting sounds on the testing of the electro-acoustic hearing prosthesis 102L itself (i.e., the same prosthesis). As such, in an ipsilateral arrangement, the electro-acoustic hearing prosthesis 102L may be configured to perform both sound processing operations to present testing sounds to a recipient, as well as the ability to perform ipsilateral remediation operations (i.e., in an ipsilateral arrangement, the testing-assistance mode includes the ability to perform sound processing of test sounds, as needed). As described further below, FIG. 2A illustrates contralateral remediation operations, while FIG. 2B illustrates ipsilateral remediation operations.

Again referring to electro-acoustic hearing prosthesis 102L, in the testing-assistance mode, the one or more processors 120L of the electro-acoustic hearing prosthesis 102L are configured to execute testing remediation logic 130L to perform one or more testing ipsilateral and/or contralateral remediation operations. As described further below, the testing remediation operations may include, for example, ambient noise monitoring, clinical masking operations, active noise cancellation operations, or other operations that support or supplement the testing of the ipsilateral or contralateral hearing prosthesis. As used herein, "clinical masking" refers to the temporary delivery of a clinical masking sound (e.g., noise) at a predetermined level to an ear of a recipient so as to temporarily elevate the threshold of that ear. Also as used herein, "active" noise cancellation refers to a method for reducing unwanted sound by the addition of a second sound specifically designed to cancel the first sound.

The testing-assistance mode of a hearing prosthesis in accordance with embodiments presented herein, such as electro-acoustic hearing prosthesis 102L, is a selectively activated mode of the hearing prosthesis. When a hearing prosthesis in accordance with embodiments presented herein is not in the testing-assistance mode, the hearing prosthesis is configured to operate in a "sound processing mode." In the sound processing mode, the hearing prosthesis is configured to operate in accordance with the determined sound processing settings (e.g., the individualized programs, commands, data, settings, parameters, instructions, etc.) to convert received sound/audio signals into acoustical and/or electrical stimulation that is delivered to the recipient. The sound processing mode is the primary/default mode for the hearing prosthesis.

FIGS. 1A-1D illustrate arrangements in which the hearing prostheses 102L and 102R include external components 104L and 104R, respectively. However, it is to be appreciated that embodiments of the present invention may be implemented in hearing prosthesis having alternative arrangements. For example, embodiments of the present invention may be implemented in so-called "totally implantable" hearing prostheses, meaning that all components of the hearing prosthesis are configured to be implanted under skin/tissue of a recipient. Because all components of a totally implantable hearing prosthesis are implantable, the hearing prosthesis operates, for at least a finite period of time, without the need of an external device and/or to program the hearing prosthesis. An external device can be used to, for example, charge an internal power source (battery) of the totally implantable hearing prosthesis. As such, the arrangements of FIGS. 1A-1D are illustrative of one of many arrangements in which embodiments presented herein may be implemented.

A hearing prosthesis in accordance with embodiments presented herein may be configured to perform one or more ipsilateral and/or contralateral testing remediation operations in a clinical setting or in the recipient's home or other remote (i.e., non-clinical) setting. FIG. 2A is a schematic diagram illustrating contralateral remediation operations in a "remote" or "testing anywhere" arrangement where a recipient, clinician, caregiver, etc. (collectively and generally referred to herein as "users") enables a hearing prosthesis to perform the testing remediation operations outside of a clinical setting. FIG. 2B is a schematic diagram illustrating ipsilateral remediation operations in the same remote arrangement of FIG. 2A. In these remote arrangements of FIGS. 2A and 2B, the testing remediation operations enable surrounding noises to be controlled without the need for additional audiological equipment.

Referring first to FIG. 2A, shown is a first hearing prosthesis 202L and second hearing prosthesis 202R that are each worn by a recipient 250. For ease of description, the hearing prostheses are electro-acoustic hearing prostheses that are each substantially similar to electro-acoustic hearing prosthesis 102L and 102R described above with reference to FIGS. 1A-1D. As such, also for ease of description, the details of the electro-acoustic hearing prostheses 202L and 202R have been omitted from FIG. 2A. The recipient 250 includes a left ear 251L (including outer, middle, and inner ear) and a right ear 251R (again including outer, middle, and inner ear). At least the recipient's left ear 251L has residual hearing.

In the example of FIG. 2A, the right ear 251R and/or the second hearing prosthesis 202R are to be tested/evaluated in some manner (e.g., the second hearing prosthesis 202R is to be fitted to the recipient 250). As such, test stimulation is to be delivered to the recipient 250 via the right ear 251R. The second hearing prosthesis 202R is sometimes referred to herein as the "tested hearing prosthesis" 202R, while the right ear is sometimes referred to as the "tested ear." In FIG. 2A, the test stimulation delivered to the recipient is generally represented by arrow 252. The test stimulation 252 may be acoustical stimulation, electrical stimulation, or mechanical stimulation (vibration). For ease of illustration, FIG. 2A is described with reference to test stimulation 252 generated by hearing prosthesis 202R (i.e., aided stimulation). However, it is to be appreciated that the techniques presented herein may be used with unaided test stimulation (i.e., test stimulation delivered without a hearing prosthesis).

The test stimulation 252 is generated based on test material. The test material can be delivered from the external device 256 (e.g., stream the test material directly to the hearing prosthesis, via free-field signals emitted by the external device 256, etc.), from within the memory of the hearing prosthesis 202R, synthesized within the hearing prosthesis 202R, etc. The test material can also be automatically adapted to the test currently run, dynamically ramped up or down based on test/time progress, etc. For example, clinical masking noise may be delivered to the higher functioning ear in a unilateral fitting, with the intention to train the fitted ear in using the aid.

In order to ensure that the testing of the hearing prosthesis 202R is largely unaffected by distracting sounds perceived via the residual hearing of the recipient's left ear 251L, the first hearing prosthesis 202L is configured to operate in a "testing-assistance" mode. In the testing assistance mode, the hearing prosthesis 202L performs testing remediation operations that, in presence of the residual hearing, at least reduce the effect of distracting sounds on the testing of the hearing prosthesis 202R. When operating in the testing-assistance mode, the first hearing prosthesis 202L is sometimes referred to herein as the "testing-assistance" or "support" prosthesis.

As noted, in the example of FIG. 2A the tested hearing prosthesis 202R delivers test stimulation 252 to the right ear 251R of the recipient. For example, the recipient 250 may listen to test material (e.g., from a hearing test to be performed on a regular basis). In order to ensure the recipient 250 is not distracted by, for example, ambient/background noise, tinnitus noise, an uncontrolled environment, etc., the support hearing prosthesis 202L performs one or more testing remediation operations. For example, the support hearing prosthesis 202L may perform active noise cancellation in the presence of ambient noise or may deliver clinical masking stimulation to the contralateral ear 251L. In FIG. 2A, the delivery of remediation stimulation (e.g., clinical masking sounds, noise cancelling sounds, etc. to reduce the effect of the distracting sounds on the testing of hearing prosthesis 202R) is generally represented by arrow 254. In this example, the remediation stimulation 254 may be acoustical stimulation, electrical stimulation, mechanical stimulation, etc.

Referring next FIG. 2B, shown is only the first hearing prosthesis 202L which, as noted, is substantially similar to electro-acoustic hearing prosthesis 102L described above. In the example of FIG. 2B, the left ear 251L and/or the first hearing prosthesis 202L are to be tested/evaluated in some manner (e.g., the first hearing prosthesis 202L is to be fitted to the recipient 250). As such, test stimulation is to be delivered to the recipient 250 via the left ear 251L (i.e., the first hearing prosthesis 202L is the tested hearing prosthesis and the left ear 251L is the tested ear). In FIG. 2B, the test stimulation delivered to the recipient is generally represented in FIG. 2 by arrow 257. The test stimulation 255 may be acoustical stimulation, electrical stimulation, or mechanical stimulation (vibration). For ease of illustration, FIG. 2B is described with reference to test stimulation 257 generated by hearing prosthesis 202L (i.e., aided stimulation). However, it is to be appreciated that the techniques presented herein may be used with unaided test stimulation (i.e., test stimulation delivered without a hearing prosthesis).

The test stimulation 257 is generated based on test material. The test material can be delivered from the external device 256 (e.g., stream the test material directly to the hearing prosthesis, via free-field signals emitted by the external device 256, etc.), from within the memory of the hearing prosthesis 202L, synthesized within the hearing prosthesis 202L, etc. The test material can also be automatically adapted to the test currently run, dynamically ramped up or down based on test/time progress, etc. For example, clinical masking noise may be delivered to the higher functioning ear in a unilateral fitting, with the intention to train the fitted ear in using the aid.

In order to ensure that the testing of the hearing prosthesis 202L is largely unaffected by distracting sounds perceived via the residual hearing of the recipient's left ear 251L, the first hearing prosthesis 202L is configured to operate in a "testing-assistance" mode. In the testing assistance mode, the hearing prosthesis 202L performs testing remediation operations that, in presence of the residual hearing, at least reduce the effect of distracting sounds on the testing of the hearing prosthesis 202L.

As noted, in the example of FIG. 2B the tested hearing prosthesis 202L delivers test stimulation 257 to the left ear 251L of the recipient. In order to ensure the recipient 250 is not distracted by, for example, ambient/background noise, tinnitus noise, an uncontrolled environment, etc., the hearing prosthesis 202L also performs one or more testing remediation operations. For example, the hearing prosthesis 202L may perform active noise cancellation in the presence of ambient noise or may deliver clinical masking stimulation to the ipsilateral ear 251L. In FIG. 2B, the delivery of remediation stimulation (e.g., clinical masking sounds, noise cancelling sounds, etc. to reduce the effect of the distracting sounds on the testing of hearing prosthesis 202L) is generally represented by arrow 259. In this example, the remediation stimulation 259 may be acoustical stimulation, electrical stimulation, mechanical stimulation, etc.

As noted, in the examples of FIGS. 2A and 2B, the hearing prosthesis 202L operates in the testing-assistance mode to perform testing remediation operations. However, the testing-assistance mode is a selectively activated mode of the hearing prosthesis 202L and the hearing prosthesis 202L is also configured to operate in a "sound processing mode." In the sound processing mode, the hearing prosthesis 202L is configured to operate in accordance with the determined sound processing settings (e.g., the individualized programs, commands, data, settings, parameters, instructions, etc.) to convert received sound/audio signals into acoustical and/or electrical stimulation that is delivered to the recipient. The sound processing mode is the primary/default mode for the hearing prosthesis 202L.

As noted, in the embodiment of FIG. 2B the hearing prosthesis 202L may both deliver test stimulation to the recipient and perform testing remediation operations. As such, FIG. 2B illustrates that, when the hearing prosthesis 202L is in the testing assistance mode, the hearing prosthesis 202L may also operate in accordance with the determined sound processing settings (e.g., the individualized programs, commands, data, settings, parameters, instructions, etc.) to convert received sound/audio signals into acoustical and/or electrical stimulation that is delivered to the recipient.

In the examples of FIGS. 2A and 2B, the hearing prostheses 202L and 202R are controlled using an external device 256. The external device 256 may be, for example, a mobile device (e.g., smart phone), computer, or other consumer electronic device with which the hearing prostheses 202L and 202R are configured to communicate. FIGS. 2A and 2B illustrate examples in which the hearing prostheses 202L and 202R are each configured to communicate with the external device 256 via a wireless connection (i.e., the hearing prostheses 202L and 202R include wireless transceivers 255L and 255R, respectively, which enable wireless connectivity for the respective prosthesis). However, in other embodiments, the hearing prostheses 202L and 202R are also or alternatively configured to communicate with the external device 256 via a wired connection (e.g., the hearing prostheses 202L and 202R each include an input/output port that can be electrically connected to a port of the external device 256).

As noted, the testing-assistance mode is a selectively activated mode for the hearing prostheses 202L. The testing-assistance mode is only activated when the hearing prostheses 202L is configured to support or assist the contralateral or ipsilateral testing of a hearing prosthesis (i.e., testing of the contralateral hearing prosthesis 202R or testing of the ipsilateral hearing prosthesis 202L). The hearing prostheses 202L may remain in the testing-assistance mode until the mode is deactivated, a predetermined period of time has passed, etc.

The testing-assistance mode of hearing prostheses 202L may be activated or deactivated in a number of different manners. In one embodiment, the testing-assistance mode is activated or deactivated via a user interface 258L (e.g., one or more buttons, a touch screen, etc.) of the hearing prostheses 202L. In other embodiments, the testing-assistance mode is activated or deactivated via a user interface 260 of the external device 256 where, in response to one or more user inputs, the external device 256 sends signals to the hearing prostheses 202L to switch the prosthesis from the sound processing mode to the testing-assistance mode.

In other embodiments, the testing-assistance mode of hearing prostheses 202L may be automatically activated or deactivated by the hearing prostheses 202L or the hearing prostheses 202R. For example, in one embodiment, the hearing prostheses 202L and the hearing prostheses 202R may be configured to communicate with one another either directly or via the external device 256 (e.g., using the external device 256 as a wireless relay/router). In such embodiments, when the hearing prostheses 202R initiates testing operations, the hearing prostheses 202R may send a message/notification to the hearing prostheses 202L to initiate/activate the testing-assistance mode. Once testing has been completed, the hearing prostheses 202R may send another message/notification to the hearing prostheses 202L to deactivate the testing-assistance mode. The testing could be triggered by context (e.g., a recipient is in a situation more suitable for testing than other situations), or on a regular basis (e.g., the recipient is tested every 6 months or other interval), etc.

The specifics of the testing remediation operations performed by the support hearing prosthesis 202L may also be set/determined in a number of different manners. In one embodiment, the testing remediation operations are set by the support hearing prosthesis 202L itself. For example, the one or more processors within the support hearing prosthesis 202L may be configured to perform environmental noise monitoring to detect and analyze ambient sound signals before the testing of hearing prosthesis 202R. In certain such embodiments, if the support hearing prosthesis 202L detects ambient noise, the one or more processors within the support hearing prosthesis 202L may then configure, for example, the active cancelling operations performed by the hearing prosthesis 202L based on the attributes (e.g., frequency, level, bandwidth, degree of autocorrelation, etc.) of the detected ambient noise. In other such embodiments, if the support hearing prosthesis 202L detects ambient noise, the support hearing prosthesis 202L may make a determination as to whether or not the testing of hearing prosthesis 202R can be performed in the given environment (i.e., determine whether the ambient noise is too loud to achieve acceptable test results).

In certain embodiments, the support hearing prosthesis 202L may be configured to perform environmental noise monitoring to analyze ambient sound signals during the testing of hearing prosthesis 202R in order to monitor whether the surrounding noise remains sufficiently low during the test or if the ambient noise likely affected the results of the testing. If the support hearing prosthesis 202L determines that the noise level is/was too high (e.g., greater than a predetermined threshold at one or more frequencies) during the test, then the support hearing prosthesis 202L can initiate the generation of an audible or visible notification to the user indicating that perception of the test stimulation 252 or 257 by the recipient 250 was likely affected by the ambient noise perceived at the left ear 251L of the recipient. The audible or visible notification, which could be delivered via the support hearing prosthesis 202L, the tested hearing prosthesis 202R, and/or the external device 256, may suggest that the test be repeated, indicate that the ambient noise is too high to accurately perform the testing of hearing prosthesis 202R, etc.

As a result of the above environmental noise monitoring at support hearing prosthesis 202L, the testing of hearing prosthesis 202R need not be performed in a particularly controlled acoustic environment since interfering ambient/background noises can be measured and removed/cancelled, up to a certain degree. Therefore, the combination of environmental noise monitoring and noise cancellation or clinical masking extends the range of environments in which the tests can be run. Additionally, the confidence in the test may be high, since the environmental noise monitoring indicates whether the environment is/was suitable for the test to be run.

In other embodiments, the testing remediation operations are set by the external device 256 based on user inputs. For example, using a user interface (e.g., one or more buttons, a touch screen, etc.) of the external device 256, a user may set parameters (e.g., timing, frequency, level, modulation characteristics, bandwidth, curve shape in time domain, etc.) of the active noise cancellation to be performed at the hearing prostheses 202L, the parameters (e.g., timing, frequency, level, modulation characteristics, bandwidth, curve shape in time domain, etc.) of the clinical masking signals to be delivered, etc. The parameters of the noise cancellation, clinical masking, or other operations may be matched specifically to the stimulation delivered to the ear under test. For example, in one embodiment, the hearing prosthesis 202L may be made aware of the frequency of the test stimulation and the active noise cancellation is applied at least in the frequency bands associated with the test stimulation.

In still other embodiments, the testing remediation operations are set by the tested hearing prosthesis 202R via a wireless communication channel/link between the hearing prostheses 202R and 202L. For example, the tested hearing prosthesis 202R may provide the parameters of the noise cancellation to be performed at the hearing prostheses 202L, parameters of the clinical masking signals to be delivered, etc.

As noted, the support hearing prosthesis 202L may perform a number of different testing remediation operations. In one embodiment, the support hearing prosthesis 202L may perform acoustic noise (e.g., ambient noise) masking, tinnitus masking, etc., perform active acoustic noise cancellation. As noted above, clinical masking refers to the temporary delivery of a clinical masking sound (e.g., noise) at a predetermined level to an ear of a recipient so as to temporarily elevate the threshold of that ear. Also as noted above, active noise cancellation refers to a method for reducing unwanted sound by the addition of a second sound specifically designed to cancel the first sound.

The remote arrangement of FIGS. 2A and 2B enable prosthesis testing to occur, for example, in the presence of tinnitus, with uncontrolled ambient noise present, etc. Additionally, this or other remote arrangements may be used for a number of different purposes. For example, the remote arrangements in accordance with embodiments presented herein may enable recipients to self-administer rehabilitation regimes (e.g., hearing exercises with the a hearing prosthesis), enable recipients to run assessments away from home, enable candidacy tests for prospective recipients (e.g., applied in the waiting room of a clinic to speed up the clinical appointment), enable intra-operative measures following initial implantation, etc.

Figure 3:
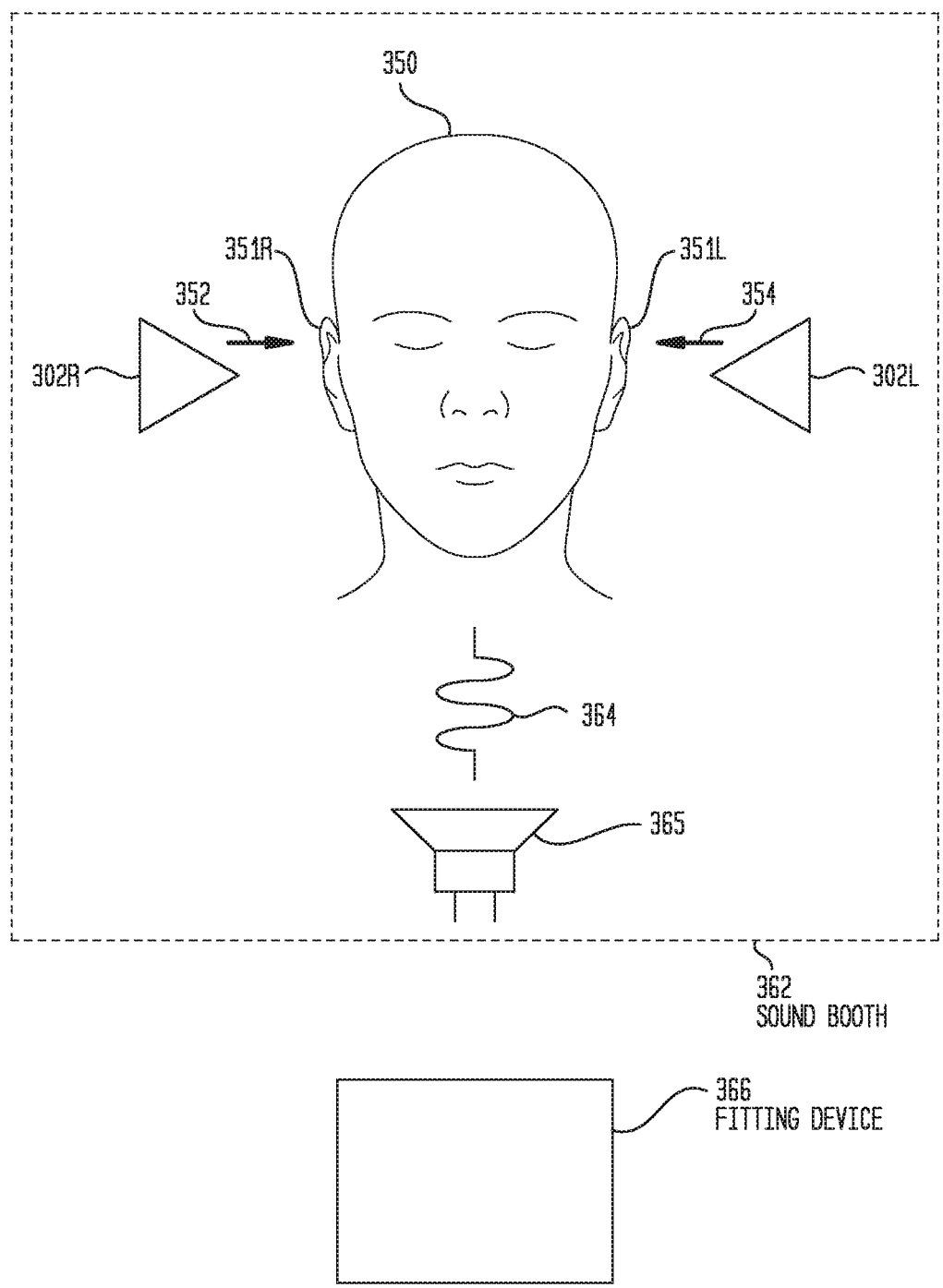
FIG. 3 is a schematic diagram illustrating implementation of the techniques presented herein, according to certain embodiments.

FIGS. 2A and 2B have been described as a remote arrangement in which the testing of a hearing prosthesis can occur outside of a clinical setting. However, it is also to be appreciated that the arrangements of FIGS. 2A and 2B could be practiced in a clinical setting where a caregiver or a medical practitioner (e.g., clinician, audiologist, etc.) makes use of the external device 256. FIG. 3 illustrates another arrangement in which the embodiments presented herein are used in a clinical setting. Merely for ease of illustration, FIG. 3 is described with reference to contralateral remediation operations.

More specifically, FIG. 3 illustrates a first hearing prosthesis 302L and second hearing prosthesis 302R that are worn by a recipient 350. For ease of description, the hearing prostheses are electro-acoustic hearing prostheses that are each substantially similar to electro-acoustic hearing prostheses 102L and 102R described above with reference to FIG. 1. As such, also for ease of description, the details of the electro-acoustic hearing prostheses 302L and 302R have been omitted from FIG. 3. The recipient 350 includes a left ear 351L (including outer, middle, and inner ear) and a right ear 351R (again including outer, middle, and inner ear). At least the recipient's left ear 351L includes residual hearing.

In the example of FIG. 3, the second hearing prosthesis 302R is to be tested/evaluated in some manner (e.g., fitted to the recipient 350) and, as such, is configured to deliver test stimulation to the recipient 350. The second hearing prosthesis 302R is sometimes referred to herein as the "tested hearing prosthesis" 302R and the test stimulation delivered to the recipient is generally represented in FIG. 3 by arrow 352.

In order to ensure that the testing of the hearing prosthesis 302R is largely unaffected by distracting sounds detected via the residual hearing of the recipient's left ear 351L, the first hearing prosthesis 302L is configured to operate in a "testing-assistance" mode. In the testing assistance mode, the hearing prosthesis 302L performs testing remediation operations that, in presence of the residual hearing, at least reduce the effect of distracting sounds on the testing of the hearing prosthesis 302R. When operating in the testing-assistance mode, the first hearing prosthesis 302R is sometimes referred to herein as the "testing-assistance" or "support" prosthesis.

As noted, in the example of FIG. 3 the tested hearing prosthesis 302R delivers test stimulation 352 to the right ear 351R of the recipient 350. In this example, the recipient 350 is located in a sound booth 362 and the test stimulation 352 is generated based on free-field test sounds/signals 364 emitted by a receiver 365 located in the sound booth. That is, the hearing prosthesis 302R is configured to detect the free-field signals 364 and to convert the free-field signals 364 into the test stimulation 352. The resulting testing stimulation 352 may be acoustical stimulation, electrical stimulation, mechanical stimulation, etc.

Since, as noted, the recipient has residual hearing, it is possible that the free-field signals 364 could also be detected at the left ear 351L and perceived by the recipient via the residual hearing, which could interfere with the testing of the hearing prosthesis 302R. As such, in order to ensure the recipient testing of the hearing prosthesis 302R is not affected by perception of the free-field signals 364 at the left ear 351L, the support hearing prosthesis 302L performs one or more testing remediation operations to cancel and/or mask the free-field signals 364. For example, the support hearing prosthesis 302L may perform active noise cancellation of the free-field signals 364 and/or may deliver clinical masking stimulation to the contralateral ear 351L. In FIG. 3, the delivery of remediation stimulation (e.g., clinical masking sounds, noise cancelling sounds, etc.) is generally represented by arrow 354. In this example, the remediation stimulation 354 may be acoustical stimulation, electrical stimulation, mechanical stimulation, etc.

As noted, the support hearing prosthesis 302L operates in the testing-assistance mode to perform testing remediation operations. However, the testing-assistance mode is a selectively activated mode of the hearing prosthesis 302L and the hearing prosthesis 302L is also configured to operate in a "sound processing mode." In the sound processing mode, the hearing prosthesis 302L is configured to operate in accordance with the determined sound processing settings (e.g., the individualized programs, commands, data, settings, parameters, instructions, etc.) to convert received sound/audio signals into acoustical and/or electrical stimulation that is delivered to the recipient. The sound processing mode is the primary/default mode for the hearing prosthesis 302L.

In the example of FIG. 3, the hearing prostheses 302L and 302R, as well as the receiver 365, are controlled via fitting system 366. The fitting system 366 may be, for example, a computer with which the hearing prostheses 302L and 302R and the receiver 365 are configured to communicate (e.g., wirelessly or via a wired connection).

Similar to the above embodiments of FIG. 2, the testing-assistance mode of hearing prostheses 302L may be activated or deactivated in a number of different manners (e.g., via user interface at the hearing prostheses 302L, in response to one or more user inputs at the fitting system 366 indicating it is time to test, etc.). Also similar to the above embodiments of FIG. 2, the specifics of the testing remediation operations performed by the support hearing prosthesis 302L may also be set/determined in a number of different manners (e.g., set by the support hearing prosthesis 302L itself, set by the fitting system 366 based on practitioner inputs, by the tested hearing prosthesis 302R, etc.). Stated differently, the parameters of the noise cancellation to be performed at the hearing prostheses 302L, the parameters of the clinical masking signals to be delivered, etc., can be determined by the hearing prostheses 302L itself and/or provided to the hearing prostheses 302L by another device. As noted, in certain embodiments the parameters of the noise cancellation, clinical masking, or other operations may be matched specifically to the stimulation delivered to the ear under test.

FIGS. 2A, 2B, and 3 illustrate various arrangements for implementation of the integrated testing remediation techniques presented herein. It is to be appreciated that FIGS. 2A, 2B, and 3 are illustrative and that the integrated testing remediation techniques presented herein may be implemented in a large number of arrangements. Table 1, below, provides a list of several specific example implementations for the integrated testing remediation techniques presented herein. More specifically, Table 1 includes combinations of: (1) environments in which the techniques presented herein may be implemented, (2) the type of tests performed within the environment, (3) operations performed at the car under test, (4) the condition of the contralateral ear (i.e., the ear that is not under test), and (5) the contralateral ear operations (i.e., the testing remediation operations performed at the ear that is not under test).

| Clinical Environment | Test type | Ear under test Operations | Contralateral ear Condition | Contralateral ear Operations |
|---|---|---|---|---|
| Anywhere | Self-assessment | Deliver test stimulation and perform active noise cancellation (ANC) | Residual hearing | Perform Clinical masking or ANC |
| Anywhere | Self-assessment | Deliver test stimulation and perform ANC | Tinnitus | Perform Clinical masking |
| Sound booth | Aided gains, unilaterally | Deliver test stimulation and perform ANC | Residual hearing | Perform Clinical masking |
| Clinic | Central test, e.g. Stapedius Reflex | Deliver test stimulation, pilot tones, and perform ANC | Residual hearing | Perform ANC |

As noted, Table 1 is illustrative and that the integrated testing remediation techniques presented herein may be used to support numerous different hearing prosthesis tests in a number of different environments. It is also to be appreciated that the testing remediation operations performed at the ear under test and/or the contralateral ear may take a number of different forms as determined by the needs of the particular recipient. That is, as described elsewhere herein, the testing remediation operations may be customized for the particular recipient. Described below are several additional examples in which the techniques presented herein may be implemented and customized for a particular recipient. For ease of illustration, these examples will be described with reference to the system 100 of FIGS. 1A-1D, where the electro-acoustic hearing prosthesis 102R is under-test (i.e., electro-acoustic hearing prosthesis 102R is the tested hearing prosthesis), while the electro-acoustic hearing prosthesis 102L is the support hearing prosthesis.

Example 1: Cross Hearing

The problem of cross hearing occurs when the non-tested ear incidentally hears the test signals that are being delivered to the ear under test. This occurs, in particular, when there is a difference in the hearing impairment between the two ears that is greater than the interaural attention, which in certain cases may be approximately 10 decibel (dB). To counter this problem, in embodiments presented herein the electro-acoustic hearing prosthesis 102L delivers an acoustic clinical masking signal to the non-tested ear 151L, substantially simultaneously with delivery of the test stimulation to the tested ear 151R. The clinical masking signal serves to temporarily elevate the hearing threshold of the non-tested ear 151L at the test frequency and thus prevents the non-tested ear from inadvertently hearing the test signal.

As noted, the test signal is delivered via the electro-acoustic hearing prosthesis 102R (or alternatively a hearing aid), while the clinical masking signal is delivered via electro-acoustic hearing prosthesis 102L. In these embodiments, an external device in communication with at least the electro-acoustic hearing prosthesis 102L calculates the required output volume of the clinical masking signal, which must arrive louder than the recipient's bone conduction threshold on the non-tested ear. The external device also determines the test signal volume, and initiates the simultaneous delivery of the test signal and the clinical masking signal. The bone conduction threshold can be predetermined from, for example, previous and recent tests, direct measurement, databases, etc.

In summary, Example 1 illustrates an embodiment in which the testing remediation operations are the delivery of clinical masking signals to the contralateral ear (i.e., the ear not under test). The clinical masking signal is a narrow-band signal having a frequency that corresponds to the frequency of the test stimulation. The level of the clinical masking signal arriving is greater than the bone conduction threshold on the other side, where the difference is dependent on the receiver used at the test ear.

Example 2: Contralateral Tinnitus

The problem of contralateral tinnitus occurs when the tinnitus that originates in the non-tested ear interferes with the ability of the ear under test to hear/concentrate on the test signal. To counter this problem, in embodiments presented herein, the electro-acoustic hearing prosthesis 102L delivers a clinical masking signal to the non-tested ear 151L. In one embodiment, the clinical masking signal is noise having a bandwidth that substantially matches the bandwidth of the tinnitus. In contrast with the cross hearing example, the clinical masking signal that is used to avoid interference due to contralateral tinnitus is not dependent on any measurements taken from the tested ear 151R. However, it is noted that embodiments presented herein may deliver a clinical masking signal for both contralateral tinnitus and cross hearing.

The tinnitus masking level can be determined from previous audiometry which aims to determine frequency, bandwidth and masking level for any tinnitus present. In summary, Example 2 illustrates an embodiment in which the testing remediation operations are the delivery of clinical masking signals to the contralateral ear (i.e., the ear not under test). The clinical masking signal has a bandwidth that that substantially matches the bandwidth of the tinnitus, and a frequency that substantially matches that of the test stimulation.

Example 3: Ambient Noise

The problem of ambient noise occurs because both the tested and non-tested ears can detect uncontrolled acoustic noise which may interfere with the calibration of, or attention to, the test stimulation. To counter this problem, in embodiments presented herein, the electro-acoustic hearing prosthesis 102R applies an active noise control algorithm to the audio signal processing associated with the acoustic output (i.e., the receiver). The degree of noise attenuation must be sufficient to reduce the volume of the ambient noise to less than that of the test signal. As such, the ambient sound is first or simultaneously assessed to determine whether or not the resulting attenuation will be sufficient. In one example, the ambient sound is monitored and the recipient is advised when a test can occur. The location of the microphone used to determine the ambient noise can be on the hearing prosthesis 102R, the hearing prosthesis 102L, or an external device, but a location as close to the pinna as possible is preferred. In certain such embodiments, when proceeding to the test, the recipient can be informed that the test will also block out ambient noise, so recipients should expect not to hear what is going on around them.

In summary, Example 3 illustrates that ambient sound can additionally be assessed so as to determine whether or not the resulting active noise attenuation will be sufficient to the purpose. If the active noise attenuation is determined to be sufficient, the noise cancellation can be performed at the ear under test 151R and/or the contralateral ear 151L.

Example 4: Bimodal Fitting

The techniques presented herein may also be used in a bimodal fitting process, where the recipient is fitted with a cochlear implant at one ear and a hearing aid at the second ear. In one such arrangement, a closed set phoneme test, or other test material, may be administered to both ears of the recipient. The gain in the hearing aid may be adjusted based on phoneme discrimination pairs, where the active noise cancellation permits only frequencies in the test phoneme to be heard over the background sound.

Figure 4:
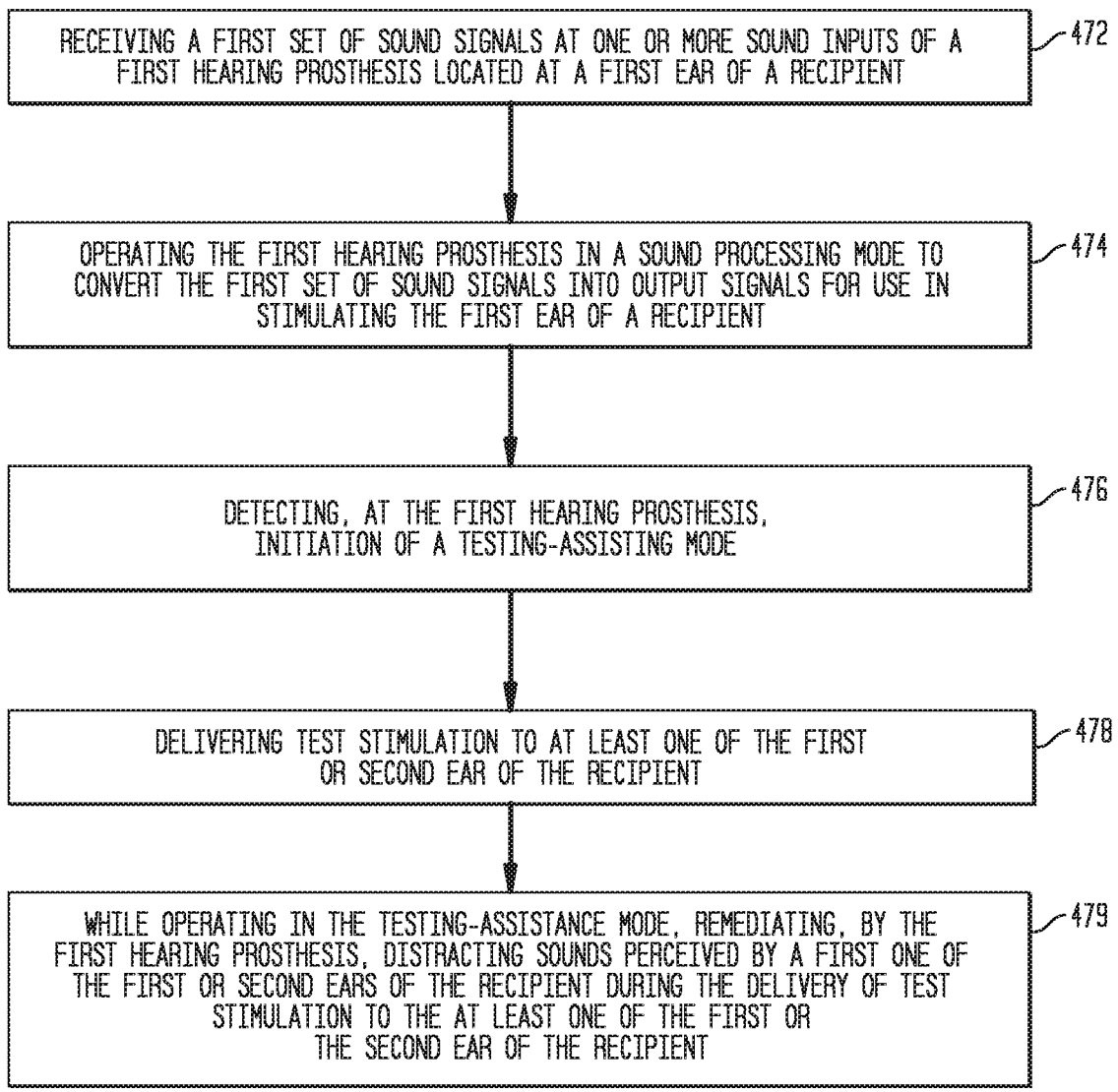
FIG. 4 is a flowchart of a method, according to certain embodiments.

FIG. 4 is a flowchart of a method 470 in accordance with certain embodiments presented herein. Method 470 begins at 472 where a first set of sound signals is received at one or more sound inputs of a first hearing prosthesis located at a first ear of a recipient. At 474, the first hearing prosthesis operates in a sound processing mode to convert the first set of sound signals into output signals for use in stimulating the first ear of a recipient. At 476, the first hearing prosthesis detects initiation of a testing-assistance and, at 478, test stimulation is delivered to at least one of the first or a second ear of the recipient. At 479, while operating in the testing-assistance mode, the first hearing prosthesis remediates distracting sounds perceived by a first one of the first or second ears of the recipient during the delivery of test stimulation to the at least one of the first or second ear of the recipient.

Figure 5:
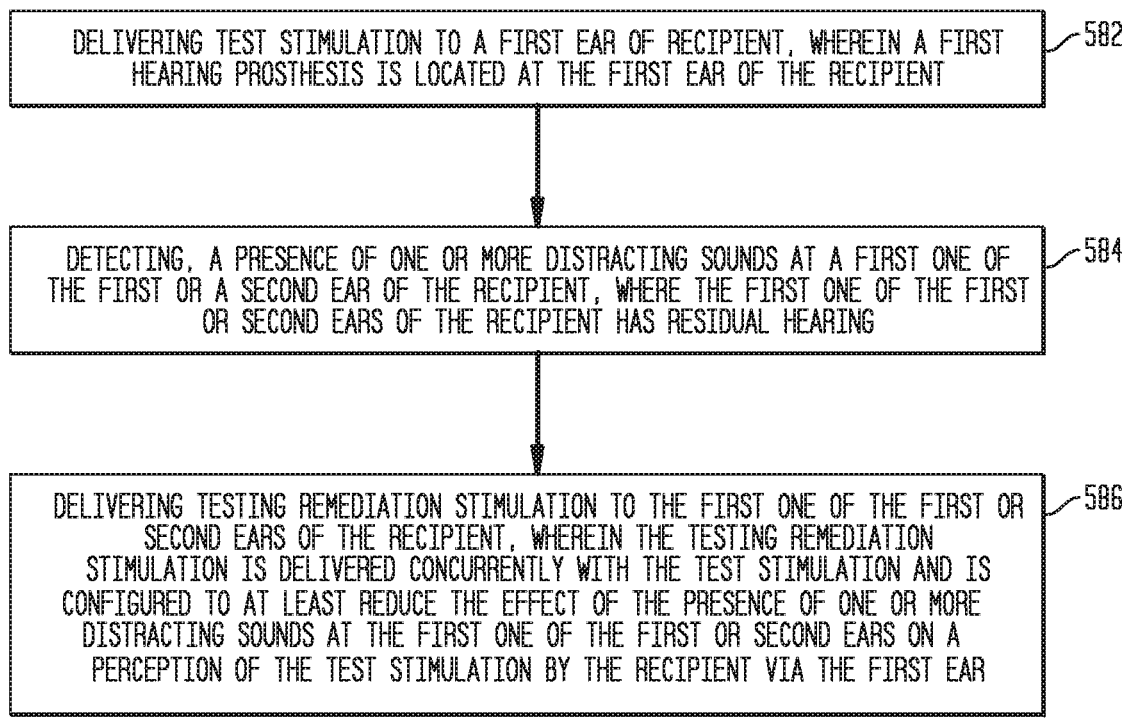
FIG. 5 is a flowchart of a method, according to certain embodiments.

FIG. 5 is a flowchart of a method 580 in accordance with certain embodiments presented herein. Method 580 begins at 582 where test stimulation is delivered to a first ear of a recipient, wherein a first hearing prosthesis is located at the first ear of the recipient. At 584, a presence of one or more distracting sounds at a first one of the first or a second ear of the recipient is detected, where the first one of the first or second ears of the recipient has residual hearing. At 586, testing remediation stimulation is delivered to the first one of the first or second ears of the recipient, wherein the testing remediation stimulation is delivered concurrently with the test stimulation and is configured to at least reduce the effect of the presence of one or more distracting sounds at the first one of the first or second ears on a perception of the test stimulation by the recipient via the first ear.

It is to be appreciated that the above embodiments are not mutually exclusive and may be combined with one another in various arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
    receiving a first set of sound signals at one or more sound inputs of a first hearing device located at a first ear of a recipient;
    operating the first hearing device in a sound processing mode to convert the first set of sound signals into output signals for use in stimulating the first ear of a recipient;
    while operating in an ipsilateral testing-assistance mode, delivering, by the first hearing device, test stimulation to the first ear of the recipient;
    while operating in the ipsilateral testing-assistance mode, detecting, by the first hearing device, at least a first sound in an environment of the recipient other than the test stimulation and performing a first type of sound remediation on the first ear of the recipient during the delivering of the test stimulation in response to the detecting the at least first sound; and
    while operating in a contralateral testing assistance mode, detecting, by the first hearing device, at least a second sound in the environment of the recipient and performing, by the first hearing device, a second type of sound remediation on the first ear of the recipient in response to detecting the at least second sound, wherein the second type of sound remediation is different from the first type of sound remediation.

2. The method of claim 1, wherein the performing of the first type of sound remediation comprises:
    delivering clinical tinnitus masking stimulation to the first ear of the recipient.

3. The method of claim 1, wherein the performing of the first type of sound remediation comprises masking ambient noise at the first ear of the recipient.

4. The method of claim 3, wherein masking ambient noise comprises performing active noise cancellation to reduce a level of the ambient noise at the first ear of the recipient.

5. The method of claim 3, wherein detecting the at least first sound comprises monitoring a level of the ambient noise at least one of prior to or during delivery of the test stimulation to the first ear of the recipient.

6. The method of claim 5, further comprising:
    determining, based on a level of the ambient noise during the delivery of the test stimulation to, that perception of the test stimulation by the recipient was likely affected by the ambient noise; and
    initiating generation of a notification to a user indicating that perception of the test stimulation by the recipient was likely affected by the ambient noise.

7. The method of claim 5, wherein the performing of the first type of remediation in response to detecting the at least first sound comprises:
    generating remediation stimulation based on the level of the ambient noise; and
    delivering the remediation stimulation to the recipient.

8. The method of claim 1, wherein performing of the second type of sound remediation includes detection and remediation of test stimulation generated by a second hearing device.

9. A first hearing device, comprising:
one or more sound inputs; and
one or more processors configured to:
- operate in a sound processing mode to convert sound signals received at the one or more sound inputs into output signals for use in stimulating a first ear of a recipient,
- selectively operate in a first testing-assistance mode to perform test sound generation and one or more testing remediation operations to support testing of the first hearing device, wherein the one or more testing remediation operations are based upon the one or more sound inputs, and
- selectively operate in a second testing-assistance mode to perform test remediation of test sounds generated by a second hearing device located at a second ear of the recipient, wherein the remediation of the test sounds generated by the second hearing device are based upon the one or more sound inputs detected by the first hearing device, wherein the remediation of the test sounds generated by the second hearing device are different than the one or more testing remediation operations to support testing of the first hearing device.

10. The first hearing device of claim 9, wherein to selectively operate in the second testing-assistance mode, the one or more processors are configured to:
- remediate distracting sounds perceived at the first ear of the recipient during delivery of test stimulation to the second ear of the recipient via the second hearing device.

11. The first hearing device of claim 10, wherein to remediate distracting sounds perceived at the first ear of the recipient during delivery of test stimulation to the second ear of the recipient via the second hearing device, the one or more processors are configured to:
- deliver testing remediation stimulation to the first ear of the recipient,
- wherein the testing remediation stimulation is delivered concurrently with delivery of the test stimulation to the second ear of the recipient and is configured to at least reduce an effect of a perception of the distracting sounds at the first ear of the recipient on a perception of the test stimulation by the recipient via the second ear.

12. The first hearing device of claim 10, wherein the distracting sounds perceived at the first ear of the recipient include ambient noise perceived at the first ear of the recipient.

13. The first hearing device of claim 12, wherein remediating the distracting sounds comprises:
- delivering clinical noise masking stimulation to the first ear of the recipient to mask the ambient noise.

14. The first hearing device of claim 9, wherein the one or more testing remediation operations of the first testing-assistance mode do not remediate the test sounds generated by the first hearing device.

* * * * *

UNITED STATES PATENT AND TRADEMARK OFFICE
CERTIFICATE OF CORRECTION

PATENT NO. : 11,924,612 B2
APPLICATION NO. : 16/753640
DATED : March 5, 2024
INVENTOR(S) : Jan Patrick Frieding et al.

Page 1 of 1

It is certified that error appears in the above-identified patent and that said Letters Patent is hereby corrected as shown below:

On the Title Page
Item (57) ABSTRACT:
Line 9, please replace "located at a second car of the recipient." with --located at a second ear of the recipient.--

In the Specification
Column 1, Line 19, please replace "the inner car," with --the inner ear,--
Column 1, Line 57, please replace "first car of a recipient;" with --first ear of a recipient;--
Column 2, Line 3, please replace "a second car of the recipient," with --a second ear of the recipient,--
Column 2, Line 66, please replace "severe sensorineural loss in the first car, mild or" with --severe sensorineural loss in the first ear, mild or--
Column 5, Line 27, please replace "prosthesis 102L at a left car 151L" with --prosthesis 102L at a left ear 151L--
Column 6, Line 20, please replace "positioned in or near the recipient's outer car." with --positioned in or near the recipient's outer ear.--
Column 11, Line 35, please replace "delivered to the recipient 250 via the left car 251L" with --delivered to the recipient 250 via the left ear 251L--
Column 16, Line 60, please replace "(3) operations performed at the car under" with --(3) operations performed at the ear under--
Column 19, Line 17, please replace "the noise cancellation can be performed at the car" with --the noise cancellation can be performed at the ear--
Column 19, Line 52, please replace "sounds at a first one of the first or a second car" with --sounds at a first one of the first or a second ear--

Signed and Sealed this
Sixteenth Day of September, 2025

Coke Morgan Stewart
*Acting Director of the United States Patent and Trademark Office*